(12) United States Patent
Johnston

(10) Patent No.: US 11,826,499 B2
(45) Date of Patent: Nov. 28, 2023

(54) SYSTEM FOR TREATING AIR

(71) Applicant: CEC Technologies, Inc., Downers Grove, IL (US)

(72) Inventor: William R. Johnston, Downers Grove, IL (US)

(73) Assignee: CEC TECHNOLOGIES, INC., Downers Grove, IL (US)

( * ) Notice: Subject to any disclaimer, the term of this patent is extended or adjusted under 35 U.S.C. 154(b) by 0 days.

(21) Appl. No.: 17/665,408

(22) Filed: Feb. 4, 2022

(65) Prior Publication Data

US 2022/0241451 A1 Aug. 4, 2022

Related U.S. Application Data

(60) Provisional application No. 63/145,805, filed on Feb. 4, 2021.

(51) Int. Cl.
*A61L 9/20* (2006.01)
*F24F 3/16* (2021.01)

(52) U.S. Cl.
CPC ........ *A61L 9/20* (2013.01); *F24F 3/16* (2013.01); *A61L 2209/14* (2013.01)

(58) Field of Classification Search
CPC .......... A61L 9/20; A61L 2209/14; F24F 3/16
See application file for complete search history.

(56) References Cited

U.S. PATENT DOCUMENTS

| | | | |
|---|---|---|---|
| 6,221,314 B1* | 4/2001 | Bigelow | A62B 29/00 422/186 |
| 9,522,210 B2* | 12/2016 | Worrilow | A61L 9/20 |
| 2004/0005252 A1 | 1/2004 | Siess | |
| 2004/0047776 A1 | 3/2004 | Thomsen | |
| 2006/0057020 A1 | 3/2006 | Tufo | |
| 2008/0086994 A1 | 4/2008 | Descotes et al. | |
| 2008/0093210 A1 | 4/2008 | Edwards | |
| 2012/0118150 A1 | 5/2012 | Brizes | |
| 2012/0207647 A1* | 8/2012 | Kim | A61L 9/00 422/107 |

(Continued)

FOREIGN PATENT DOCUMENTS

CN 107131585 A 9/2017

OTHER PUBLICATIONS

"GermAwayUV High Occupancy 150 Watt Wall Mountable Air Purifier and Sanitizer—Manual Guide." 5 pages, retrieved from https://www.cureuv.com/ on or before Feb. 4, 2022.

(Continued)

*Primary Examiner* — Sean E Conley
(74) *Attorney, Agent, or Firm* — STEPTOE & JOHNSON LLP; Carl B. Wischhusen; Benjamin Holt

(57) ABSTRACT

A system for treating air includes a first vent and second vent and an air passage in fluid communication between the first and second vents. Air is drawn into the first vent, moved through the air passage, and expelled from the second vent. The air passage includes an ultraviolet-C ("UV-C") chamber, comprising a UV-C source, and a filter located after the UV-C chamber in the air passage and exposed to the UV-C source. Air moved through the air passage is treated by the UV-C source and then the filter. Such system may be used to treat air containing coronavirus particles.

31 Claims, 5 Drawing Sheets

(56) References Cited

U.S. PATENT DOCUMENTS

| | | | |
|---|---|---|---|
| 2014/0020561 A1* | 1/2014 | Aery | B01D 46/60 |
| | | | 55/467 |
| 2019/0059242 A1* | 2/2019 | Bogner | A01G 9/18 |
| 2019/0063763 A1* | 2/2019 | Kleinberger | A61L 2/022 |

OTHER PUBLICATIONS

"GermAwayUV Centurion High Occupancy 240 Watt Ultraviolet Air Sanitizer and Disinfection System Operation Manual." 10 pages, retrieved from https://www.cureuv.com/ on or before Feb. 4, 2022.

"GermAwayUV High Occupancy Wall Mountable Air Purifier and Sanitizer" 11 pages, retrieved from https://www.cureuv.com/ on or before Feb. 4, 2022.

"GermAwayUV High Occupancy 240 Watt 694 CFM UV Air Sanitizer and Disinfection System." 4 pages, retrieved from https://www.cureuv.com/ on or before Feb. 4, 2022.

"Chapter 62, Ultraviolet Air and Surface Treatment," 2019 ASHRAE Handbook—HVAC Applications, 2019, pp. 62.1-62.17. https://www.ashrae.org/file%20library/technical%20resources/covid-19/i-b_a19_ch62_uvairandsurfacetreatment.pdf.

Storm et al., "Rapid and complete inactivation of SARS-Cov-2 by ultraviolet-C irradiation," Scientific Reports, 2020, 10:22421, 5 pages. https://www.nature.com/articles/s41598-%20020-79600-8.

PCT Search Report and Written Opinion from PCT/US22/15372, dated Apr. 27, 2022, 9 pages.

\* cited by examiner

SYSTEM FOR TREATING AIR

CLAIM OF PRIORITY

This application claims priority from U.S. Provisional Application No. 63/145,805, filed on Feb. 4, 2021, which is incorporated by reference in its entirety.

BACKGROUND

There is concern regarding shared air in any area where people come into contact. Such concern includes potential transmission of airborne illnesses as well as general sanitation and hygiene issues. This concern affects any space where people gather, including facilities used for work, recreation, residential living, shopping, dining, or other services. Present air treatment systems may not effectively sterilize or filter the air, for example, to remove harmful airborne pathogens, or effectively treat air in a large space or target area.

DETAILED DESCRIPTION

Figure 1:
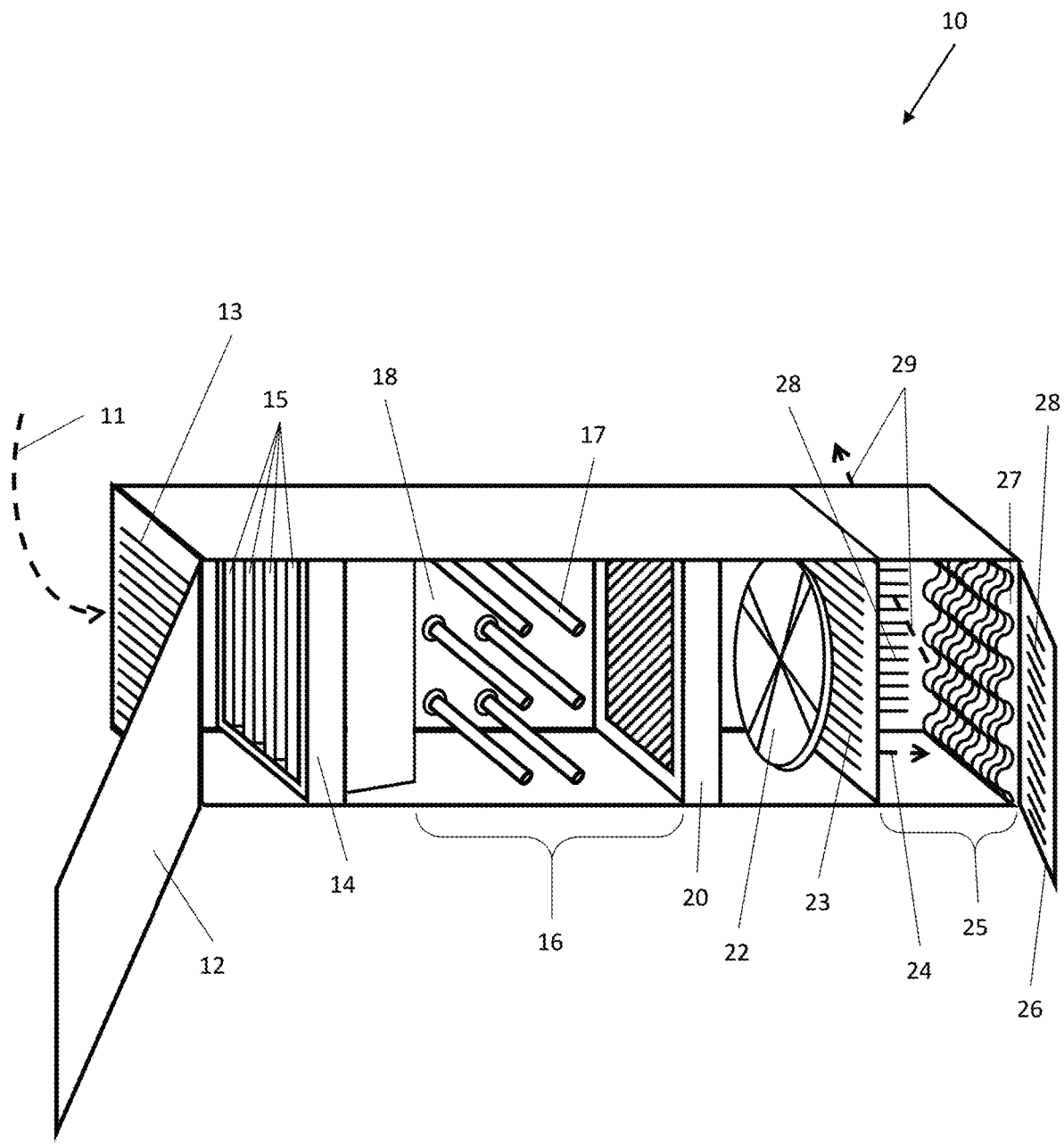
FIG. 1 is a perspective view of an exemplary HVAC sterilization and filtration unit.

The following disclosure provides different embodiments, or examples, for implementing different features of the subject matter. Specific examples of components, features, arrangements, or steps are described below to simplify the present disclosure. These are, of course, merely examples and are not intended to be limiting.

The air treatment systems of the present invention utilize both sterilization and filtration. In one embodiment, sterilization can be performed by one or more ultraviolet-C ("UV-C") sources that emit UV-C light (i.e., 200 to 280 nm), such as a bulb, LED, lamp, or other UV-C source or emitter. (References to a UV-C "bulb" herein should be understood to encompass, or be substitutable with, any source or emitter of UV-C light.) In one embodiment, filtration can be performed by one or more filters with a sufficiently high Minimum Efficiency Reporting Value ("MERV") rating and/or one or more High Efficiency Particulate Air ("HEPA") filters.

The air treatment systems include heating, ventilation, and air conditioning ("HVAC") units to sufficiently treat large occupied spaces, specialized designs to treat air at tables or other surfaces, specialized designs to create a virtual barrier for a target personal space, and specialized designs to prevent air from reaching or escaping target areas.

Aerosol can be defined as particles, or tiny solids, dispersed in air or gas. For example, viruses, such as coronaviruses (e.g., SARS or COVID-19) or influenza, can be spread through aerosol droplets. The combination of UV-C light and filtration with HEPA rating and/or a sufficiently high MERV rating consistently and constantly sterilizes and removes such particles and droplets from air, resulting in clean, sterilized air that can safely be injected back into a space or area.

In one embodiment, UV-C bulbs can effectively sanitize and disinfect air to eliminate viruses, including coronaviruses and influenza, and additionally mold and bacteria. In one example, the SARS virus can be inactivated by at least 15 minutes of UV-C light exposure. In another example, UV-C light can disinfect 99% of certain viruses and bacteria (i.e., influenza A, vaccinia, coxsackievirus, *staphylococcus* A, tuberculosis, *Legionella*) in an average time of two minutes at a distance of 11 feet and an average time of three minutes at a distance of 17 feet.

In one embodiment, one or more UV-C bulbs can be implemented in a UV-C chamber. For example, tube-shaped UV-C bulbs can be positioned across the chamber such that the ends of the tubes are on either side of the chamber, and the surface of the tube faces perpendicular to the direction of airflow through the chamber. In one example, tube-shaped UV-C bulbs in the chamber can be implemented on a rack.

In one embodiment, a UV-C chamber can be a compact space in an air passage and can include UV-C bulbs of sufficient number and intensity to sufficiently sterilize all air that passes through the UV-C chamber, and thus the air passage, in a single or first pass. In one example, a compact, high-intensity, single-pass UV-C chamber has a kill area length of 8 inches and cross-sectional area of 1.653 square feet. This chamber, which may treat air at an airflow rate of 500 cubic feet per minute (CFM), can include 3 UV-C bulbs—each with 21 Watts, a UV-C wavelength of 253.7 nm, and an intensity of 50 $\mu W/cm^2$—such that over 99.6% of microbial population in the air is sterilized by one pass through the chamber. In another example, a UV-C chamber has a kill area length of 16 inches and cross-sectional area of 2.77 square feet. This chamber, which may treat air at an airflow rate of 1400 CFM, can include 8 UV-C bulbs—each with 48 Watts, a UV-C wavelength of 253.7 nm, and an intensity of 120 $\mu W/cm^2$—such that 100% of microbial population in the air is sterilized by one pass through the chamber. In another example, a UV-C chamber has a kill area length of 16 inches and cross-sectional area of 4 square feet. This chamber, which may treat air at an airflow rate of 2500 CFM, can include 8 UV-C bulbs—each with 48 Watts, a UV-C wavelength of 253.7 nm, and an intensity of 120 $\mu W/cm^2$—such that 100% of microbial population in the air is sterilized by one pass through the chamber.

In one embodiment, one or more UV-C bulbs can be implemented in a hydroxyl radical generator. For example, a hydroxyl radical generator can use UV-C light to create hydroxyl radicals that can sterilize air (e.g., by killing viruses, such as COVID-19, in air droplets or particles). In one embodiment, a hydroxyl radical generator can react titanium dioxide with UV-C light to generate hydroxyl radicals and/or can react ozone with UV-C light to generate hydroxyl radicals. For example, titanium dioxide can be provided via paint, such as titanium dioxide pigment in paint applied to one or more inner surfaces of a UV-C chamber of the hydroxyl radical generator and thus exposed to UV-C light in the chamber, to create hydroxyl radicals. For example, ozone can be provided via an ozone-producing bulb installed or positioned in a UV-C chamber of the hydroxyl radical generator, such that ozone emitted by the ozone bulb is exposed to UV-C light in the chamber, to create hydroxyl radicals. In one embodiment, a hydroxyl radical generator sterilizes air using both UV-C light and hydroxyl radicals created using UV-C light.

In one embodiment, filtration of a sufficient MERV rating and/or filtration with a HEPA filter can catch and remove tiny particles from air. In one example, a filter with a MERV rating of 13 or higher can trap over 75% of particles as small as 0.3 to 1.0 microns. For example, a MERV 13 filter can remove the following contaminates in air: pollen, dust, lint, dust mites, debris, pet dander, mold spores, car fumes, smoke, bacteria, virus carriers, and small allergens. For reference, a sneeze droplet is found to be 5 to 10 microns. In one example, a HEPA filter can capture 99.97% of air particles (e.g., dust, pollen, mold, bacteria, virus carriers, or other air particles) that are 0.3 microns (worst case) and can capture air particles smaller or larger than 0.3 microns at a higher efficiency. A MERV 13 filter or higher and/or a HEPA filter can thus catch most airborne particles.

In one embodiment, filtration can be performed by a V-bank filter. For example, a V-bank filter can provide high-efficiency filtration and higher filter media area than a standard box filter. A V-bank filter can include a frame and two or more V-bank packs, for example, oriented or shaped in a V-shape, where the "V" is open to, or faces, the direction from which air travels to pass through the V-bank filter. In one example, a MERV filter or HEPA filter can be in the form of a V-bank filter, i.e., a V-bank filter can include MERV and/or HEPA filtration.

In one embodiment, the present invention includes a system that pulls in or removes untreated air from a target space or area, treats the air with a combination of UV-C light and MERV 13+ and/or HEPA filtration to sterilize, disinfect, filter, and clean the air, and outputs the air, for example, back into the target space or area; away from the target space or area; and/or into the room or general space in which the target space or area is located.

A target space or area can be a room or large open space. A more particular target space or area can be a person; a table or other surface, or a portion thereof; a personal space, such as an office space, cubicle, booth, desk, work station, counter space, locker, chair, or exercise equipment; or any other area or space where persons are in close proximity and/or one or more persons seek to not exchange unsanitary or unfiltered air with one or more other persons. In one example, untreated air is removed from a room, and treated air is output back into the room. In one example, untreated air is removed from a specific target area, and treated air is output at or near the same target area. In one example, untreated air is removed from a specific target area, and treated air is output in the general area or room containing the target area.

In one embodiment, the air treatment system can be contained in a single machine or unit, such as an HVAC unit or air handler. In one embodiment, the air treatment system can be a system containing one or more intake vents, one or more output vents, and one or more ducts or air passageways between, and in fluid communication with, the input and output vents. For example, untreated air can be removed from, and treated air can be output at, one or more target areas using one or more vents, and the one or more vents for removal and/or output of air can have different sizes, locations, and orientations (facing directions). In one embodiment, UV-C sterilization, MERV filtration (e.g., high-rated MERV filtration such as MERV 13+ filtration), and/or HEPA filtration can be performed at or proximate to one or more input vents, at or proximate to one or more output vents, and/or at or along a portion of a duct or air passage, for example, connecting or in direct or indirect fluid communication between said input vent(s) and output vent(s). In one example, an air treatment system contains a single air treatment unit, which performs both UV-C sterilization and HEPA and/or high-rated MERV filtration. In one example, an air treatment system contains multiple air treatment units. In one embodiment, UV-C sterilization is performed by 1, 2, 3, 4, 5, 6, 7, 10, 15, or more than 15 UV-C bulbs. In one embodiment, filtration is performed by 1, 2, 3, 4, 5, 7, 10, 15, or more than 15 MERV or HEPA filters. In one embodiment the MERV filter is rated 8, 9, 10, 11, 12, 13, 14, 15, or 16. In one embodiment the MERV filter or HEPA filter has a thickness or depth of 1, 2, 3, 4, 5, 6, 7, 8, 9, 10, 11, 12, 16, 20, 24, or more than 24 inches.

In one embodiment, one or more pre-filters or initial filters, such as a V-bank filter and/or lower-rated MERV filter (e.g., MERV 1 to MERV 10 filter), is located before one or more UV-C bulbs and/or before a separate subsequent main filter, such as a HEPA filter or high-rated MERV filter (e.g., MERV 13+ filter), in an air passage, so that air passing through the air passage is first filtered by the initial filter(s) and is then sterilized by the UV-C bulb(s) and/or filtered by the separate subsequent main filter. For example, this can decrease the amount of air particles that reach and must be sterilized by the UV-C bulb(s) and can decrease the amount of air particulates captured by the separate subsequent main filter over a given period of time, thus increasing the efficiency and decreasing the replacement frequency of the separate subsequent main filter.

In one embodiment, one or more UV-C bulbs, such as UV-C bulbs in a UV-C chamber, can be positioned immediately prior to a filter in an air passage, such as the highest-rated main filter in the passage (e.g., a HEPA or highly-rated MERV filter), based on the direction of airflow, such that air flowing through the air passage is first sterilized by UV-C and then filtered. For example, this relative positioning of a UV-C chamber and subsequent filter decreases the amount of unsterilized or unsanitary air filtered by the main filter and thus decreases the risk (e.g., biohazard or infection risk) imposed on a user when replacing, disposing of, or otherwise handling the used filter.

In one embodiment, one or more UV-C bulbs, such as UV-C bulbs in a UV-C chamber, can be positioned in an air passage such that a filter in the air passage is exposed to the UV-C light emitted by the UV-C bulb(s) or chamber. For example, this positioning and exposure sterilizes the filter, as well as particles captured in and by the filter, using the UV-C light emitted by the bulb(s) or chamber. For example, this sterilization of the filter decreases the risk (e.g., biohazard or infection risk) imposed on a user when replacing, disposing of, or otherwise handling the used filter.

FIG. 1 shows a perspective view of an exemplary HVAC sterilization and filtration unit 10. HVAC unit 10, or a similar embodiment, can turn over the air in a space (i.e., completely replace, recycle, or treat the entire volume of air of the space) at a sufficient rate to reduce the risk of airborne pathogens (e.g., COVID-19) spreading through the air of the space and can additionally control and limit odors, smoke, dust, pollen, and other potential aerosol issues. Examples of such spaces include rooms or other indoor areas in homes, schools, gyms, nursing homes, libraries, hotels, commercial facilities, and convention halls.

HVAC unit 10 is shown with removable body side panel 12, of the body of HVAC unit 10, removed such that the interior components of the body of HVAC unit 10 can be observed. HVAC unit 10 contains an intake vent 13 on one end of the unit 10, an output vent 23 on another end of the unit 10, and an air passage in fluid communication between intake vent 13 and output vent 23. Intake air 11 is pulled or drawn into HVAC unit 10 via intake vent 13 by blower 22. Blower 22 can be any type of device capable of drawing air into and/or propelling air through HVAC unit 10 at a sufficient air flow speed, such as a fan, vacuum, or blower. For example, blower 22 can draw air through the air passage of HVAC unit 10 at an airflow rate of 500, 750, 1000, 1200, 1400, 1600, 1800, 2000, 2250, 2500, 2750, 3000, or more than 3000 CFM. In one embodiment, the HVAC unit has an airflow rate of at least 500 CFM, at least 1400 CFM, or at least 2500 CFM.

HVAC unit 10 contains an initial V-bank filter 14 through which intake air 11 is filtered. V-bank filter 14 includes multiple V-bank packs 15 in the housing of V-bank filter 14. In one example, V-bank filter 14 can include HEPA filtration or MERV filtration (e.g., MERV 8, 13, and/or 16). In one example, V-bank filter 14 can have a depth of 8, 9, 10, 11, 12, 13, 14, or more than 14 inches. Such an initial filter or pre-filter can remove dust, oils, and other particles before air is treated by UV-C light or by one or more separate, subsequent, higher-rated filters. Such an initial filter or pre-filter can be at, proximate to, or part of intake vent 13. In other embodiments, HVAC unit 10 can include a different pre-filter instead of V-bank filter 14 or can include one or more other pre-filters in addition to V-bank filter 14, for example, located between intake vent 13 and V-bank filter 14 or directly after V-bank filter 14. In other embodiments, HVAC unit 10 can include a box-style pre-filter, such as a MERV filter (e.g., MERV 5 to MERV 16, such as MERV 10, with a depth of 1 to 16 inches, such as a 1-inch or 4-inch depth) directly before or after, or in place of, V-bank filter 14.

HVAC unit 10 also contains a UV-C chamber 16 through which intake air 11 passes and is sterilized by UV-C light. UV-C chamber 16 contains 6 tube-shaped UV-C bulbs 17, oriented such that the ends of the UV-C bulbs 17 are located at the sides of the air passage through HVAC unit 10 and the tube surfaces of UV-C bulbs 17 are perpendicular to the direction of airflow through HVAC unit 10. In other embodiments, UV-C chamber 16 can have a different number, type, or arrangement of UV-C bulbs than that shown in FIG. 1. In one embodiment, UV-C bulbs 17 may emit light at 200 to 280 nm, such as about 250 to 255 nm, such as about 253.7 nm. In one embodiment, UV-C chamber 16 contains appropriate dimensions and UV-C bulbs such that UV-C chamber 16 is a high-intensity single-pass UV-C chamber that sterilizes all air drawn through UV-C chamber 16 on the first pass, based on the airflow rate through HVAC unit 10, as discussed above.

In other embodiments, HVAC unit 10 may also contain a hydroxyl radical generator through which intake air 11 passes and is sterilized using both UV-C light and hydroxyl radicals created using UV-C light. In one embodiment, UV-C chamber 16 can be a hydroxyl radical generator. For example, chamber wall 18, and/or the opposite wall, floor, or ceiling of UV-C chamber 16, can be coated with titanium dioxide paint such that UV-C light from UV-C bulbs 17 reacts with the titanium dioxide on chamber wall 18 to produce hydroxyl radicals. For example, one of UV-C bulbs 17 can be an ozone-producing bulb (e.g., at approximately 185 nm) that produces ozone that reacts with UV-C light from UV-C bulbs 17 to produce hydroxyl radicals.

HVAC unit 10 also contains a HEPA filter 20. HEPA filter 20 is positioned after UV-C chamber 16 in the air passage through HVAC unit 10, and HEPA filter 20 is the highest-rated filter in HVAC unit 10.

UV-C chamber 16 is bounded, enclosed, bordered, or limited on one end (i.e., air intake end) by V-bank filter 14 and on the other opposite end (i.e., air output end) by HEPA filter 20. For example, V-bank filter 14 is exposed to UV-C light produced by UV-C bulbs 17 in UV-C chamber 16, particularly the rear-facing side of V-bank filter 14. For example, HEPA filter 20 is exposed to UV-C light produced by UV-C bulbs 17 in UV-C chamber 16, particularly the front-facing side of HEPA filter 20.

After intake air 11 is filtered and sterilized by the treatment components of HVAC unit 10, including V-bank filter 14, UV-C chamber 16, and HEPA filter 20, the air is expelled through output vent (or exhaust or return vent) 23 as sterilized and filtered output air 24. For example, output air 24 is output into the same space or room from which intake air 11 was drawn into HVAC unit 10.

Blower 22 is positioned after HEPA filter 20 and before output vent 23, at the end of the air passage in the body of HVAC unit 10 before output vent 23. In one embodiment, this placement or positioning of blower 22 increases the efficiency of blower 22 and the airflow through HVAC unit 10 and the components along the air passage thereof. In other embodiments, blower 22 may be positioned before the initial filter or in other places in the air passage.

HVAC unit 10 may also contain an add-on muffler chamber 25, which is affixed to, and configured to receive sterilized and filtered output air 24 from, output vent 23. In other embodiments, the muffler chamber can be integrated into the body of HVAC unit 10 rather than attached as an add-on. Muffler chamber 25 can decrease the noise created by HVAC unit 10 by 6, 8, 10, 12, 14, 16, or more than 16 decibels.

Muffler chamber 25 is shown with removable muffler chamber side panel 26 removed such that the interior components of the muffler chamber 25 can be observed. Muffler chamber 25 includes sound absorbing foam 27 and serves as a sound barrier to absorb, muffle, diffuse and/or dampen sound created by HVAC unit 10. In other embodiments, muffler chamber 25 can include other sound-absorbing material(s). Sound absorbing foam 27 is positioned in muffler chamber 25 directly opposite of output vent 23 to counter noise coming from or through output vent 23, particularly noise resulting directly or indirectly from blower 22, which is positioned proximate to output vent 23 and blows air through output vent 23.

Sterilized and filtered output air 24 from output vent 23 passes through muffler chamber 25 and is expelled through muffler chamber vents 28, out of HVAC unit 10 and into the surrounding space, as represented by muffled treated output air 29. FIG. 1 shows muffler chamber vents 28 on each side of muffler chamber 25, rather than directly opposite of output vent 23 and blower 22. In other embodiments, muffler chamber vent(s) 28 can be located on the back (opposite of output vent 23), top, and/or bottom of muffler chamber 25. In other embodiments, where HVAC unit 10 does not include a muffler chamber 25, sterilized and filtered output air 24 is expelled from HVAC unit 10 directly into the surrounding space through output vent 23.

The HVAC unit can contain various combinations and arrangements of filters and UV-C chambers and/or bulbs. In one example, the HVAC unit can include, in order, a pre-filter (e.g., 1-inch depth), a V-bank MERV 16 filter (e.g., 11.5-inch depth), a UV-C chamber, and a HEPA filter (e.g., 11.5-inch depth). In one example, the HVAC unit can include, in order, a MERV 8 filter, a MERV 16 filter, a hydroxyl radical generator (including a UV-C chamber), and a HEPA filter. In one example, the HVAC unit can include, in order, a pre-filter, a MERV 8 filter, a UV-C chamber, and a MERV 15 bag filter. In one example, the HVAC unit can include, in order, a MERV 8 to MERV 10 filter (e.g., 2- to 4-inch depth), a UV-C chamber, and a MERV 13+ filter (e.g., with depth of 4+ inches, such as an 11-inch depth).

Certain combinations and arrangements of filters and UV-C chambers and/or bulbs can result in increased efficiency, effectiveness, and safety. For example, initial filters, such as V-bank filter 14, can decrease the amount of air particles that reach and must be sterilized by UV-C chamber 16 further along the air passage in HVAC unit 10, thus increasing the efficiency and effectiveness of UV-C chamber 16. Also, initial filters, such as V-bank filter 14, can decrease the amount of air particles that reach and are captured by any filter(s) (e.g., higher-rated filters) further along the air passage in HVAC unit 10, such as HEPA filter 20, thus increasing the efficiency and decreasing the replacement frequency of HEPA filter 20.

Also, for example, the positioning of UV-C chamber 16 before HEPA filter 20 in the air passage in HVAC unit 10 can sterilize air before it is filtered by HEPA filter 20, thus decreasing the amount of unsterilized air particles captured by HEPA filter 20 and decreasing the risk associated with replacing, disposing of, or otherwise handling HEPA filter 20 after use. Also, UV-C chamber 16 and HEPA filter 20 are positioned and configured such that HEPA filter 20 is exposed to UV-C light from UV-C bulbs 17 in UV-C chamber 16, thus sterilizing HEPA filter 20, as well as the particles captured by HEPA filter 20, using UV-C light, which decreases the risk associated with replacing, disposing of, or otherwise handling HEPA filter 20 after use.

In one embodiment, HVAC unit 10 is a stand-alone unit. In one embodiment, HVAC unit 10 can be a portable and/or mobile unit, for example, with a handle and/or on wheels. In one embodiment, HVAC unit 10 can be a stationary unit and, for example, can be supported from a ceiling structure (e.g., suspended) or wall mounted.

Figure 2:
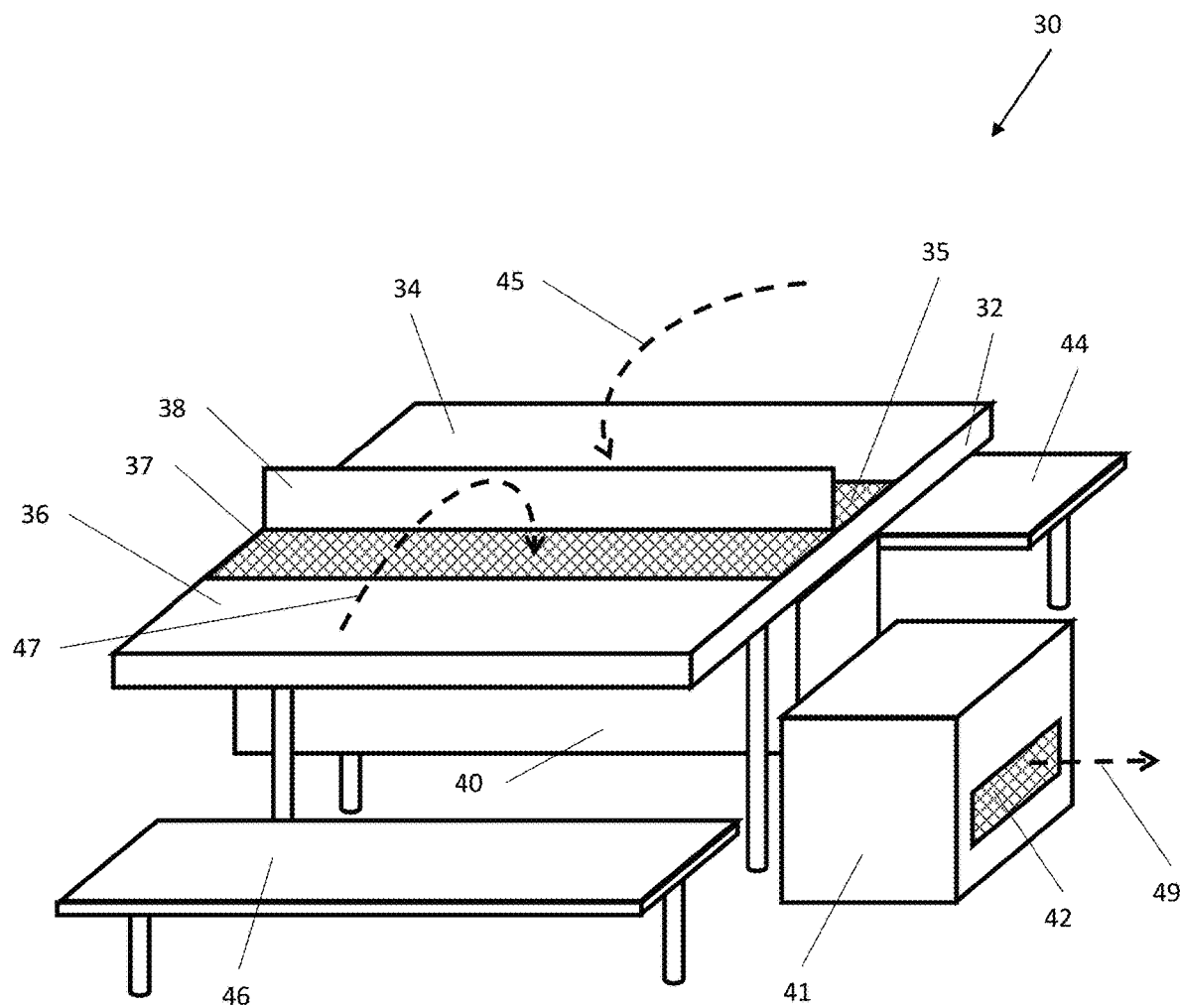
FIGS. 2-3 are a perspective view and top view, respectively, of an exemplary table air treatment system.
Figure 3:
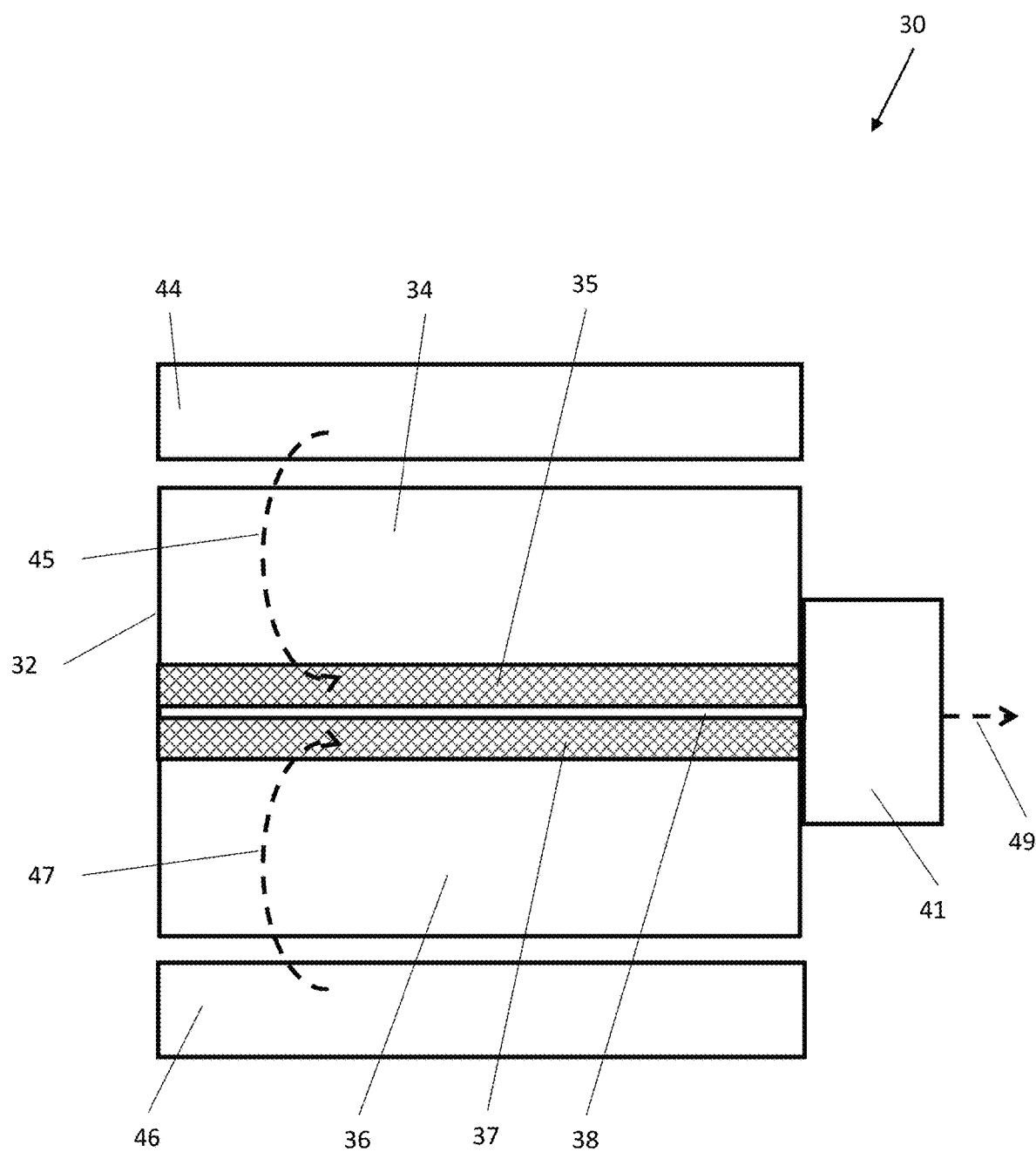

In addition to an HVAC unit implementation, the present invention may be implemented in a table or other surface. FIGS. 2-3 are a perspective view and top view, respectively, of an exemplary table air treatment system 30. Table air treatment system 30 contains a table 32 that includes a first side 34 and second side 36. Proximate to the center of table 32, where first and second sides 34, 36 adjoin, is an intake vent system made up of a single intake vent or an intake vent that is divided into first intake vent 35 and second intake vent 37. First intake vent 35 is on first side 34 of table 32, and second intake vent 37 is on second side 36 of table 32. The openings of first and second intake vents 35, 37 can be designed or covered to permit or facilitate air flow while preventing physical materials such as food from passing through the vents 35, 37. For example, first and second intake vents 35, 37 can include or be covered by a screen or perforated material. In one example, first and second intake vents 35, 37 are flush with the top surface of table 32. In another example, first and second intake vents 35, 37 can be angled to face toward first and second sides 34, 36, respectively, of table 32.

Table air treatment system 30 includes a barrier (or divider) 38 positioned between first and second intake vents 35, 37 in an upright position, i.e., perpendicular to the top surface of table 32. In one embodiment, barrier 38 can extend to a height above the top surface of table 32 such that a first person seated at first side 34 and a second person seated at second side 36 can see one another over the top of barrier 38. For example, barrier 38 can have a height of 16, 12, 10, 8, 6, or 4 inches above the top surface of table 32. In one embodiment, a portion of, or the entirety of, barrier 38 can be transparent, for example, such that a person seated at first side 34 can see a person seated at second side 36 through barrier 38. For example, barrier 38 can be partially or fully made of glass, plastic, or plexiglass. In one embodiment, where barrier 38 or a portion thereof is transparent, barrier 38 can extend to a height above the top surface of table 32 such that it completely separates a first person seated at first side 34 and a second person seated at second side 36, for example, such that the direct line of sight between the first and second persons is through the barrier 38. For example, barrier 38 can have a height of 16, 20, 24, 28, 32, 36, 40, 44, 48 or more than 48 inches above the top surface of table 32.

First and second intake vents 35, 37 lead to and are connected (e.g., in fluid communication) to under-table duct 40. And under-table duct 40, in turn, leads to and is connected (e.g., in fluid communication) to sterilization and filtration unit 41, which contains output vent 42. Table air treatment system 30 contains at least one fan, vacuum, blower, or other device, for example, in under-table duct 40 or sterilization and filtration unit 41, to draw or propel air into first and second intake vents 35, 37, through under-table duct 40, through sterilization and filtration unit 41, and out of output vent 42. In one example, system 30 contains a blower rated at 1100 CFM.

For example, first intake air 45 represents untreated air flowing from first side 34 of table 32 in the direction of second side 36, such as air expelled by a first person seated at first seat 44 (e.g., by breathing, speaking, or blowing), and second intake air 47 represents untreated air flowing from second side 36 of table 32 in the direction of first side 34, such as air expelled by a second person seated at second seat 46. Table air treatment system 30 pulls first intake air 45 down into first intake vent 35, to prevent first intake air 45 from flowing to second side 36, and pulls second intake air 47 down into second intake vent 37, to prevent second intake air 45 from flowing to first side 34. Table air treatment system 30 can draw air into first and second intake vents 35, 37 at an airflow rate sufficient to redirect and pull down first and second intake air 45, 47 without letting such air pass over first and second intake vents 35, 37, respectively. For example, air can be pulled through first and second intake vents 35, 37 into under-table duct 40 at 30-50 feet per minute (FPM); air intake at more than 50 FPM may be excessive and disruptive, and air intake at less than 30 FPM may be insufficient, for example, to prevent unclean air from passing over first and second intake vents 35, 37 from one side of table 32 to the other.

Barrier 38, in combination with air drawn down into first and second intake vents 35, 37, also directs first intake air 45 down into first intake vent 35, directs second intake air 47 down into second intake vent 37, and prevents first intake air 45 from flowing to second side 36 or second intake air 45 from flowing to first side 34.

First and second intake air 45, 47, after being drawn into and through first and second intake vents 35, 37, are drawn through under-table duct 40 to sterilization and filtration unit 41 and are then expelled from output vent 42.

Sterilization and filtration unit 41 contains at least one UV-C bulb (e.g., 4 UV-C bulbs in a UV-C chamber) and at least one filter (e.g., MERV 13+ filter or HEPA filter), to sterilize and filter air that is drawn through first and second intake vents 35, 37, under-table duct 40, and sterilization and filtration unit 41, before that air is expelled from output vent 42. For example, untreated first and second intake air 45, 47 undergo UV-C sterilization and MERV and/or HEPA filtration in sterilization and filtration unit 41 and are then expelled from output vent 42 as treated output air 49. In one example, there is a filter, such as the filters described above, located at the opening connecting the air passage of under-table duct 40 to the air passage of sterilization and filtration unit 41. The UV-C bulb(s) and filter(s) of sterilization and filtration unit 41 constantly sterilize and filter air and all particles in the air (e.g., including infected droplets in air) passing through unit 41.

In one example, sterilization and filtration unit 41 can be removably detached from under-table duct 40, such as to allow maintenance, cleaning, or replacement of parts in sterilization and filtration unit 41 or under-table duct 40, such as maintenance, cleaning, or replacement of a fan, a filter, or a UV-C bulb.

In table air treatment system 30, treated output air 49 is expelled away from the target area of table 32. Expelling air away from the target area can limit interference with airflow at, near, or on the table, such as the airflow drawn into first and second intake vents 35, 37. In other embodiments, treated output air 49 can be expelled back at, near, or in the direction of the target area table 32, such as downward from above table 32, upward out of a center portion of the top surface of table 32, or below table 32. In other embodiments, treated output air 49 can be expelled to the side of table 32, behind one or more seats at table 32, to an area distal to the table and seats, or into an HVAC system.

In other embodiments, some or all of the components, and functions, of sterilization and filtration unit 41, including one or more fans, vacuums, blowers, or other similar devices, sterilization components, filtration components, and/or output vent 42 of sterilization and filtration unit 41, can be included in, and performed by, under-table duct 40. In one such example, sterilization and filtration unit 41 can be excluded from table air treatment system 30.

In other embodiments, table 32 can be any surface at or around which two or more people can gather. For example, table 32 can be a table or surface of a different size or shape (e.g., circle, square, or rectangular), with different seating arrangements (e.g., first and second persons seated across from one another on first and second seats 44, 46; seated on the same seat on the same side of the table; or seated diagonally from each other at first and second adjoining sides of a rectangular table).

In other embodiments, table 32 can have one or more air intake (or removal) vents, such as first and second air intake vents 35, 37, of different sizes, shapes, locations, and orientations. For example, table 32 can include one or more air intake vents at a top or side edge of the table, at a corner of the table between two adjoining edges, at the center of the top surface of the table, and/or at the top surface of the table between two seating positions at the table. Such one or more air intake vents can guide untreated air into an air passage where the air is treated via UV-C sterilization and high-rated MERV or HEPA filtration and then expelled, such as the air passage formed by under-table duct 40 and sterilization and filtration unit 41.

In other embodiments, table 32 can have one or more barriers or dividers, such as barrier 38, of different sizes, shapes, locations, and orientations. For example, table 32 can include a divider along an edge or center of each air intake vent (as discussed above) or along a length of the top surface of the table that divides a first portion of the table for a first seating position at the table from a second portion of the table for a second seating position at the table (e.g., a divider that runs along the top surface of the table from a first point proximate to an edge of the table between the first and second seating positions to a second point away from the edge of the table). For example, the divider can be an airflow barrier that redirects air toward or into an air intake vent.

In one embodiment, an existing table can be retrofitted with the table air treatment system of the present invention. For example, a portion of a table top can be removed and replaced with one or more intake vents, an under-table duct can be fitted and affixed underneath the table top such that the under-table duct connects to and is in fluid communication with the one or more intake vents to receive air drawn through the intake vent(s), and sterilization and filtration components and an output vent can be added, for example, in the under-table duct or in a separate sterilization and filtration unit connected to and in fluid communication with the under-table duct.

Table air treatment system 30 can enable two or more people to eat at a table, without table dividers obstructing the view or noise transmission between them, while preventing any cough, sneeze, aerosol, droplets, or other airborne material from one person from reaching another person. The downdraft through table 32 can pull down such unclean air expelled by a person at table 32 as well as unclean air in the atmosphere of the room in which table air treatment system 30 is located. The table air treatment system 30 can constantly sterilize and filter the unclean air, and once the air has been cleaned, push it back out into the room. Additionally, with this application, table air treatment system 30 can constantly treat and recycle air in the room where it is located.

Figure 4:
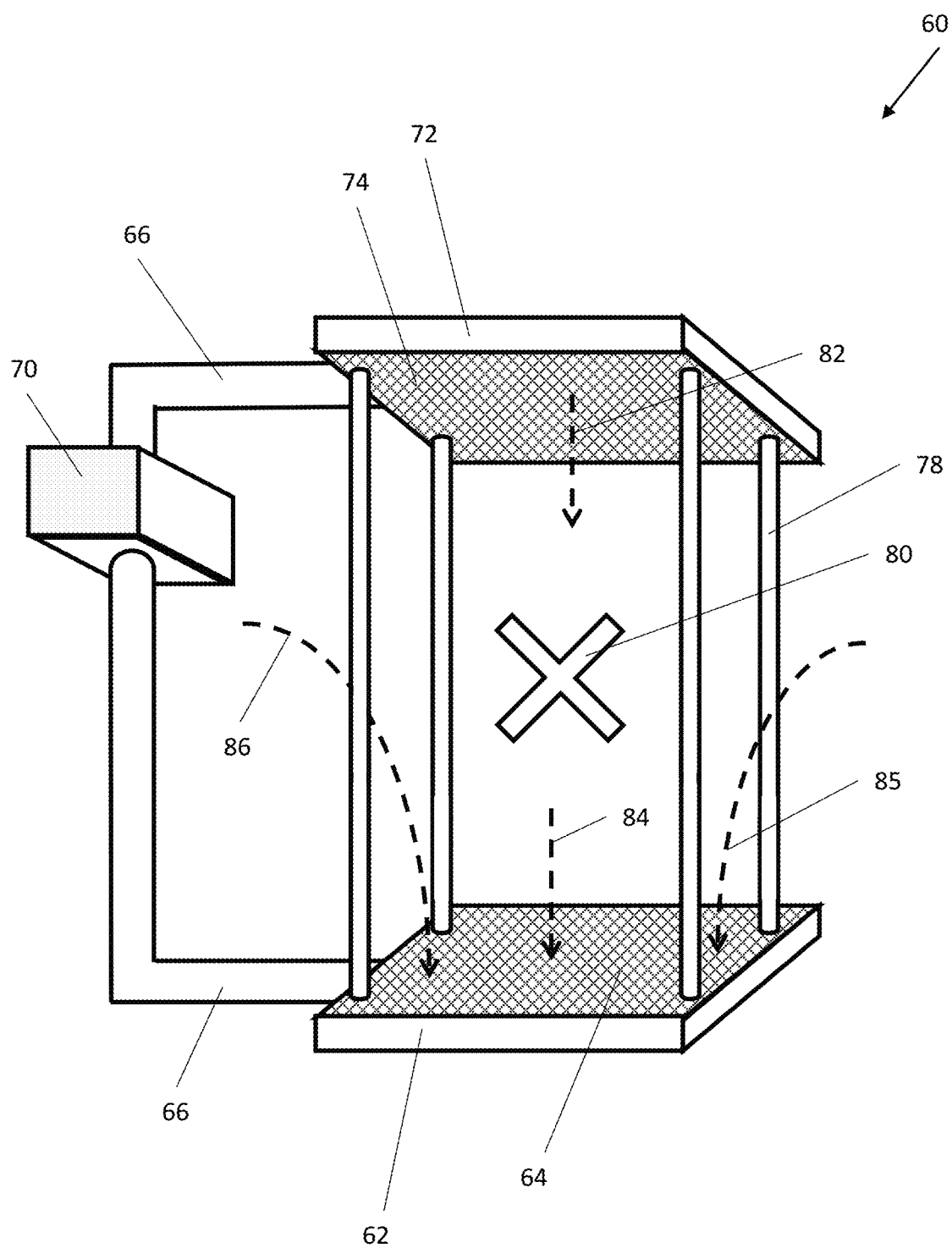
FIG. 4 is a perspective view of an exemplary virtual barrier air treatment system.

In addition to an HVAC unit implementation and a table implementation, the present invention may be implemented as a virtual barrier for a personal space. FIG. 4 is a perspective view of an exemplary virtual barrier air treatment system 60. Virtual barrier air treatment system 60 contains a lower (or bottom) intake platform 62 with intake vent 64 and an upper (or top or overhead) output unit 72 with output vent 74. Lower intake platform 62 can be even with, on top of, or below the floor. Intake vent 64 and output vent 74 are connected (e.g., in fluid communication) via an air passageway, which includes duct 66 and sterilization and filtration unit 70. Also included in system 60 is one or more fans, vacuums, blowers, and/or other devices to pull or propel air downward and into intake vent 64, through lower intake platform 62, through duct 66, through sterilization and filtration unit 70, through upper output unit 72, and downward and out of output vent 74. One or more of such fans, vacuums, blowers, and/or other devices can be contained in lower intake platform 62, duct 66, sterilization and filtration unit 70, and/or upper output unit 72.

The intake and output vents 64, 74 of lower intake platform 62 and upper output unit 72, respectively, define a target space 80. Target space 80 is above intake vent 64 of lower intake platform 62 and below output vent 74 of upper output unit 72. Upper output unit 72 is supported by four support poles 78, which indicate generally the corners of target space 80.

Sterilization and filtration unit 70 contains at least one UV-C bulb (e.g., 4 UV-C bulbs in a UV-C chamber) and at least one filter (e.g., a 4-inch MERV 13+ filter or HEPA filter), to sterilize and filter unclean air that passes through intake vent 64, lower intake platform 62, duct 66, and sterilization and filtration unit 70, before that air then passes through the remainder of duct 66, through upper output unit 72, and out of output vent 74. For example, untreated first, second, and third intake air 84, 85, 86 are pulled into intake vent 64, undergo UV-C sterilization and MERV and/or HEPA filtration in sterilization and filtration unit 70, and are then expelled from output vent 74 as treated output air 82. The UV-C bulb(s) and filter(s) of sterilization and filtration unit 70 constantly sterilize and filter air and all particles in the air (e.g., including infected droplets in air) passing through unit 70.

Target space 80 can be any space where unclean, untreated air is unwanted. In one embodiment, target space 80 can be a personal space for one or more persons, such as a work station (e.g., desk, service counter, assembly line, or operating table), workout or locker station, bed or sleeping space, cooking or eating space, or meeting space. In one embodiment, intake and output vents 64, 74 are sized and positioned such that target space 80 can accommodate such exemplary spaces.

Virtual barrier air treatment system 60 forms a "virtual barrier" around target space 80 using airflow and air treatment. In one example, first intake air 84 represents unclean air produced or originating in target space 80, and system 60 protects the environment outside of target space 80 from unclean first intake air 84 by pulling or drawing that first intake air 84 downward and into intake vent 64 before it can escape through the virtual barrier to the environment outside of target space 80. In one example, second and third intake air 85, 86 represent unclean air produced or originating outside of target space 80, and system 60 protects target space 80 from unclean second and third intake air 85, 86 by pulling or drawing that second and third intake air 85, 86 downward and into intake vent 64 such that it does not reach, for example, a person occupying target space 80. In one example, system 60 protects both target space 80 and the environment outside of target space 80 by constantly filling target space 80 with clean, treated output air 82 from output vent 74 above target space 80.

For example, if a first person sneezes or coughs while in the first person's assigned target space 80, that unclean air would not reach the environment outside of target space 80, and if a second person located outside of target space 80 sneezes or coughs toward target space 80, that unclean air would not reach the first person within target space 80. Additionally, if a sneeze or cough does escape through the virtual barrier, into or out of target space 80, then by the time that unclean air reached a person on the other side of the virtual barrier, that unclean air would be low to the ground and the person's feet, and if within the target space 80, that unclean air would quickly or instantly be pulled into intake vent 64. A person within the virtual barrier created by system 60 to protect target space 80 thus has a significantly decreased chance of catching and spreading airborne pathogens.

In one embodiment, multiple target spaces 80 can be assigned to multiple people, with each person occupying a different target space 80, and with each target space 80 protected by a separate and different virtual barrier air treatment system 60. Two or more of the multiple systems 60 can share a shared portion of duct 66, can share a shared sterilization and filtration unit 70, and/or can share a shared fan, vacuum, blower, or similar device.

In other embodiments, some or all of the components, and functions, of sterilization and filtration unit 70, including one or more fans, vacuums, blowers, or other similar devices, sterilization components, and filtration components, can be included in, and performed by, other parts of virtual barrier air treatment system 60, such as lower intake platform 62, duct 66, and/or upper output unit 72. In one such example, sterilization and filtration unit 70 can be excluded from system 60.

In other embodiments, system 60 can include one or more physical boundaries or dividers to separate part or all of target space 80 from the environment outside of target space 80. For example, a divider can be positioned at one or more corners or sides of target space 80 and can, for example, extend from lower intake platform 62 upward, such as part or all of the way to upper output unit 72. For example, such a divider can be solid or perforated.

In other embodiments, system 60 can include, in addition to or instead of intake vent 64, one or more intake vents proximate to target space 80, which can be shaped, sized, positioned, or oriented differently from intake vent 64. In other embodiments, system 60 can include, in addition to or instead of output vent 74, one or more output vents proximate to target space 80, which can be shaped, sized, positioned, or oriented differently than output vent 74. Such intake vents and output vents can remove unclean air and output clean treated air, respectively, from/to target space 80. In one embodiment, the intake vent(s) of system 60 can pull in air at an airflow rate sufficient to redirect and pull down first, second, and third intake air 84, 85, 86. For example, air can be pulled through intake vent 64 at 30-50 FPM.

Figure 5:
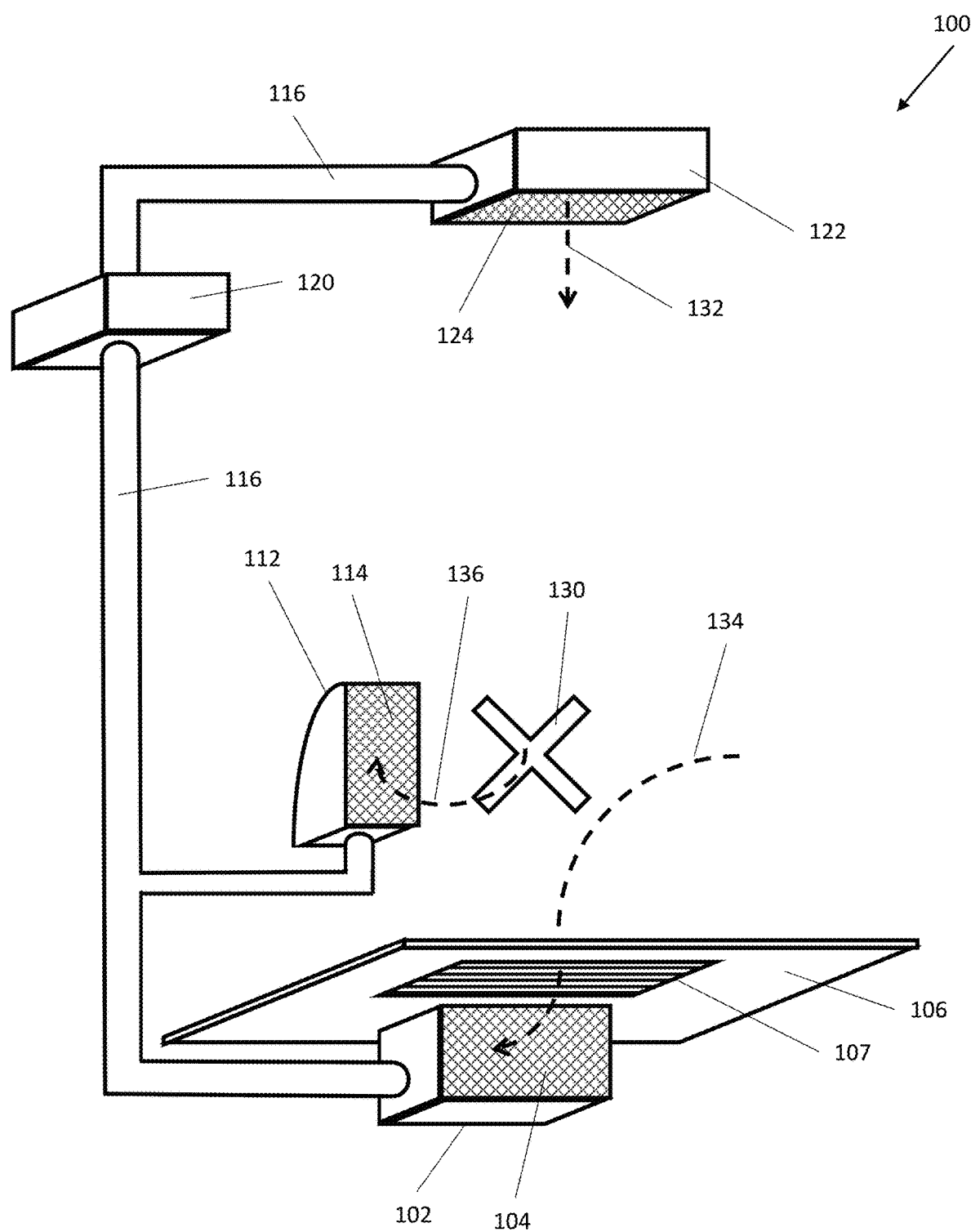
FIG. 5 is a perspective view of an exemplary targeted air treatment system.

A further implementation of the present invention, similar to the virtual barrier implementation, is an implementation for targeted air removal and treatment. FIG. 5 is a perspective view of an exemplary targeted air treatment system 100. Targeted air treatment system 100 includes first intake unit 102 with first intake vent 104, second intake unit 112 with second intake vent 114, and output unit 122 with output vent 124. First intake unit 102 is located below grate 107 in floor (or platform) 106, directly below target area (or person) 130. Second intake unit 112 is located directly behind or beside target area 130. Output unit 122 is located within the same room as target area 130.

First intake unit 102, second intake unit 112, and output unit 122 are all connected (e.g., in fluid communication) via air passageways, which include duct system 116 and sterilization and filtration unit 120. Also included in targeted air treatment system 100 is one or more fans, vacuums, blowers, and/or other devices to pull or propel air into first and second intake vents 104, 114, through duct system 116, through sterilization and filtration unit 120, through output unit 122, and out of output vent 124. One or more of such fans, vacuums, blowers, and/or other devices can be contained in first intake unit 102, second intake unit 112, duct system 116, sterilization and filtration unit 120, and/or output unit 122.

Sterilization and filtration unit 120 contains at least one UV-C bulb (e.g., 4 UV-C bulbs in a UV-C chamber) and at least one filter (e.g., a 4-inch MERV 13+ filter or HEPA filter), to filter and sterilize unclean air that passes through either first intake vent 104 and first intake unit 102 or second intake vent 114 and second intake unit 112, duct system 116, and sterilization and filtration unit 120, before that air then passes through the remainder of duct system 116, through output unit 122, and out of output vent 124. For example, untreated first and second intake air 134, 136 are pulled into first and second intake vents 104, 114, respectively, undergo UV-C sterilization and MERV and/or HEPA filtration in sterilization and filtration unit 120, and are then expelled from output vent 124 as treated output air 132. The UV-C bulb(s) and filter(s) of sterilization and filtration unit 120 constantly sterilize and filter air and all particles in the air (e.g., including infected droplets in air) passing through unit 120.

Target area 130, similar to target space 80 discussed above, can be any area, person, or thing where unclean, untreated air is unwanted. In one embodiment, target area 130 can be a personal space for one or more persons, such as a work station (e.g., desk, service counter, assembly line, or operating table), workout or locker station, bed or sleeping space, cooking or eating space, or meeting space.

First and second intake vents 104, 114 are strategically located to draw air away from target area 130. For example, first intake vent 104 of first intake unit 102 is located below target area 130, such as an employee locker, to pull unclean, first intake air 134 downwards toward the employee's feet at a constant rate, thus reducing the risk of viruses and bacteria from spreading to the employee through aerosol and pathogens in first intake air 134. That is, unclean air near the employee at target area 130 is directly removed from near the employee at target area 130 and treated, rather than waiting for that unclean air near the employee at target area 130 to be removed and treated as part of general turnover of the entire air in the room. Also, for example, second intake vent 114 of second intake unit 112 is located beside or behind target area 130, such as an employee work station, to pull unclean, second intake air 136 away from the employee and employee's work station, thus reducing the risk of viruses and bacteria from spreading from the employee to other people or materials in second intake air 136. For example, because of first and second intake vents 104, 114, a sneeze or cough from another person will not reach the employee at target area 130 and a sneeze or cough from the employee at target area 130 will not reach another person.

Then, once first and second intake air 134, 136 are removed and treated by sterilization and filtration unit 120, the treated air is recycled back out through output vent 124 as treated output air 132, for example, into the atmosphere of the room or general space in which target area 130 is located, such as at the top of the room. Thus, in addition to preventing unclean air from spreading to or from target area 130, system 100 also constantly recycles, or turns over, the air in the room in which system 100 is located.

In other embodiments, targeted air treatment system 100 can contain only first intake unit 102 and not second intake unit 112 or can contain only second intake unit 112 and not first intake unit 102. In other embodiments, there may be more than two intake units.

In one embodiment, multiple target areas 130 can be assigned, with each target area 130 protected by its own first intake unit 102 and/or second intake unit 112, and the first and second intake units 102, 112 for each target area could connect to duct system 116 such that unclean air from all first and second intake units 102, 112 is treated by sterilization and filtration unit 120 and output as clean, treated output air 132.

In other embodiments, some or all of the components, and functions, of sterilization and filtration unit 120, including one or more fans, vacuums, blowers, or other similar devices, sterilization components, and filtration components, can be included in, and performed by, other parts of targeted air treatment system 100, such as first intake unit 102, second intake unit 112, duct system 116, and/or output unit 122. In one such example, sterilization and filtration unit 120 can be excluded from system 100.

In one embodiment, the first and second intake vents 104, 114 can pull in air at an airflow rate sufficient to redirect and pull air away from target area 130. For example, air can be pulled through each of first and second intake vents 104, 114 at 30-50 FPM.

In one embodiment, targeted air treatment system 100 can include a blower to achieve a target airflow and turnover rate.

The foregoing description, for purposes of illustration and explanation, used specific nomenclature to provide a thorough understanding of the invention. However, it will be apparent to one skilled in the art that specific details are not required in order to practice the invention. Thus, the foregoing descriptions of specific embodiments of the invention are not intended to be exhaustive or to limit the invention to the precise forms disclosed; obviously, many modifications and variations are possible in view of the above teachings. The embodiments were chosen and described in order to best explain the principles of the invention and its practical applications, and they thereby enable others skilled in the art to best utilize the invention and various embodiments with various modifications as are suited to the particular use contemplated.

The invention claimed is:

1. A system for treating air comprising:
a first vent and a second vent;
an air passage in fluid communication between the first vent and the second vent, wherein air is drawn into the first vent, moved through the air passage, and expelled from the second vent;
an ultraviolet-C(UV-C) chamber comprising a UV-C source, wherein the UV-C source is arranged perpendicularly to the direction of air movement through the air passage and wherein the air moved through the air passage is treated by the UV-C source;
a main filter in the air passage, wherein the main filter is located after the UV-C chamber in the air passage and is exposed to the UV-C source such that the UV-C source sterilizes a front-facing surface of the main filter, and wherein the air moved through the air passage is treated by the main filter after being treated by the UV-C source; and
a muffler chamber connected to receive the air expelled from the second vent, wherein the muffler chamber comprises a sound-absorbing material, wherein the sound-absorbing material is positioned in the muffler chamber directly opposite of the second vent.

2. The system of claim 1, wherein the air contains coronavirus particles and the system kills such particles.

3. The system of claim 1, further comprising an initial filter located in the air passage before the UV-C chamber, wherein the air moved through the air passage is treated by the initial filter before being treated by the UV-C source and the main filter.

4. The system of claim 1, wherein the main filter is a High Efficiency Particulate Air (HEPA) filter or has a Minimum Efficiency Reporting Value (MERV) rating of at least 13.

5. The system of claim 1, further comprising a hydroxyl radical generator in the air passage, wherein the air moved through the air passage is treated by the hydroxyl radical generator.

6. The system of claim 1, further comprising a fan or blower that draws the air into the first vent, moves the air through the air passage, and expels the air from the second vent, wherein the fan or blower is positioned proximate to the second vent.

7. The system of claim 1, wherein the system has an airflow rate of at least 800 cubic feet per minute.

8. The system of claim 1, further comprising a table, wherein the first vent is located on an upper surface of the table.

9. The system of claim 8, further comprising an under-table duct, wherein the under-table duct forms a portion of the air passage.

10. The system of claim 8, further comprising a removable air treatment box, wherein the removable air treatment box forms a portion of the air passage and comprises the UV-C chamber and the main filter.

11. The system of claim 8, further comprising a fan or blower that draws air into the first vent, moves air through the air passage, and expels air from the second vent.

12. The system of claim 8, wherein the system has an airflow rate of 30 to 50 feet per minute.

13. The system of claim 8, wherein the first vent is in the center of the upper surface of the table.

14. The system of claim 13, further comprising a barrier oriented perpendicular to the upper surface of the table and positioned substantially in the middle of the first vent, such that the first vent is divided into a first portion on a first side of the barrier and a second portion on a second side of the barrier.

15. The system of claim 14, wherein the barrier is less than 6 inches in height above the upper surface of the table.

16. The system of claim 1, wherein the first vent is located at the lower end of a personal space and draws air downward from the personal space through the first vent.

17. The system of claim 16, wherein the second vent is located at the upper end of the personal space and expels treated air downward into the personal space.

18. The system of claim 16, wherein the second vent is located away from the personal space and expels treated air away from the personal space.

19. The system of claim 16, further comprising a fan or blower that draws air into the first vent, moves air through the air passage, and expels air from the second vent.

20. The system of claim 6, wherein the fan or blower is located after the main filter in the air passage and before the second vent.

21. The system of claim 1, wherein the muffler chamber comprises a muffler chamber vent and expels the air through the muffler chamber vent.

22. A system for treating air comprising:
a first vent and a second vent;
an air passage in fluid communication between the first vent and the second vent, wherein air is drawn into the first vent, moved through the air passage, and expelled from the second vent;
an ultraviolet-C(UV-C) chamber comprising a UV-C source, wherein the UV-C source is arranged perpendicularly to the direction of air movement through the air passage and wherein the air moved through the air passage is treated by the UV-C source, wherein the UV-C chamber is configured to achieve 100% sterilization of the air moved through the air passage in a single pass at an airflow rate of 2500 cubic feet per minute;
a main filter in the air passage, wherein the main filter is located after the UV-C chamber in the air passage and is exposed to the UV-C source such that the UV-C source sterilizes a front-facing surface of the main filter, and wherein the air moved through the air passage is treated by the main filter after being treated by the UV-C source; and
a muffler chamber connected to receive the air expelled from the second vent, wherein the muffler chamber comprises a sound-absorbing material.

23. The system of claim 22, wherein the air contains coronavirus particles and the system kills such particles.

24. The system of claim 22, further comprising an initial filter located in the air passage before the UV-C chamber, wherein the air moved through the air passage is treated by the initial filter before being treated by the UV-C source and the main filter.

25. The system of claim 22, wherein the main filter is a High Efficiency Particulate Air (HEPA) filter or has a Minimum Efficiency Reporting Value (MERV) rating of at least 13.

26. The system of claim 22, further comprising a hydroxyl radical generator in the air passage, wherein the air moved through the air passage is treated by the hydroxyl radical generator.

27. The system of claim 22, further comprising a fan or blower that draws the air into the first vent, moves the air through the air passage, and expels the air from the second vent, wherein the fan or blower is positioned proximate to the second vent.

28. The system of claim 27, wherein the fan or blower is located after the main filter in the air passage and before the second vent.

29. The system of claim 22, wherein the system has an airflow rate of at least 800 cubic feet per minute.

30. The system of claim 22, wherein the muffler chamber comprises a muffler chamber vent and expels the air through the muffler chamber vent.

31. The system of claim 22, wherein the sound-absorbing material is positioned in the muffler chamber directly opposite of the second vent.

* * * * *